United States Patent [19]

Di Trapani et al.

[11] Patent Number: 4,914,226

[45] Date of Patent: Apr. 3, 1990

[54] MALONIC ACID DERIVATIVES AND METHODS FOR THEIR SYNTHESIS

[75] Inventors: Romano Di Trapani; Antonio S. Verdini, both of Monterotondo, Italy

[73] Assignees: Eniricerche S.p.A., Milano; Sclavo S.p.A., Siena, both of Italy

[21] Appl. No.: 74,053

[22] Filed: Jul. 16, 1987

[30] Foreign Application Priority Data

Jul. 16, 1986 [IT] Italy ................ 21143 A/86

[51] Int. Cl.$^4$ .................................. C07C 175/65
[52] U.S. Cl. .................................. 560/157; 560/154; 560/190; 560/55
[58] Field of Search .................. 560/157, 55, 190, 154

[56] References Cited

U.S. PATENT DOCUMENTS

| | | | |
|---|---|---|---|
| 3,013,069 | 12/1961 | Wilkinson et al. | 560/55 |
| 4,439,360 | 3/1984 | Verdini et al. | 260/112.5 |
| 4,499,079 | 2/1985 | Gordon et al. | 546/165 |
| 4,816,560 | 3/1989 | Verdini et al. | 530/323 |

FOREIGN PATENT DOCUMENTS

0082568 11/1984 European Pat. Off.
0097994 9/1987 European Pat. Off.

OTHER PUBLICATIONS

Sheppard, "Peptide Synthesis," *Comprehensive Organic Chemistry*, Pergamon Press, Oxford, pp. 321-334 (1985).

Kritzler et al., *Chemical Abstracts*, vol. 61, No. 580h (1964).
Hayashi, *Chemical Abstracts*, vol. 55, No. 7304e (1961).
Oda et al., *Chemical Abstracts*, vol. 59, No. 3806g (1963).
Cohen, *Chemical Abstracts*, vol. 81, No. 63234x (1974).

*Primary Examiner*—Bruce Gray
*Attorney, Agent, or Firm*—Birch, Stewart, Kolasch & Birch

[57] ABSTRACT

The present invention refers to a new class of malonic acid derivatives of general formula I

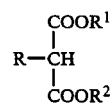

wherein $R^1$ and $R^2$, each independently, represent hydrogen or a carboxyl protecting group, and the residue R corresponds to the side-chain of the amino acids lysine, ornithine, tyrosine, cysteine, asparatic acid and glutamic acid wherein the additional functionalities are suitably protected. The new compounds of the present invention are useful for preparing analogues of biologically active peptides wherein the direction of some amide bonds in which the amino acids lysine, ornithine, tyrosine, cysteine, aspartic acid or glutamic acid are involved, has been reversed.

5 Claims, No Drawings

MALONIC ACID DERIVATIVES AND METHODS FOR THEIR SYNTHESIS

The present invention refers to a class of malonic acid derivatives of general formula I

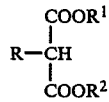

wherein $R^1$ and $R^2$, each independently, represent hydrogen or a carboxyl protecting group, e.g. a straight or, preferably, branched alkyl group containing up to 6 carbon atoms, typically ethyl, isopropyl, tert-butyl, and tert-amyl, or an aralkyl group such as benzyl or substituted benzyl, e.g. nitro-benzyl, alkoxy-benzyl, alkylbenzyl and the like, and the residue R corresponds to the side-chain of the amino acids lysine, ornithine, tyrosine, cysteine, aspartic acid and glutamic acid wherein the side-chain functionalities of said amino acids (the amino group of the basic amino acids lysine and ornithine, the hydroxyl group of tyrosine, the thiol group of cysteine and the carboxyl group of the acidic amino acids) are suitably protected.

In particular, therefore, the residue R may have one of the following chemical structures

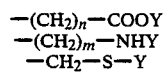

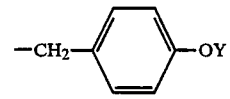

wherein n is 1 or 2, m is 3 or 4, and Y is a suitably selected protecting group.

The malonic acid derivatives of the present invention can be easily incorporated in peptide chains according to known general methods (see for instance EP-B-82568 which corresponds to U.S. Pat. No. 4,439,360, EP-A-97994, thus allowing the reversal of such bonds as X-Asp, X-Glu, X-Cys, X-Lys, X-Orn, and X-Tyr (wherein X represents any natural amino acid residue with the exclusion of proline) without side-reactions due to the presence of reactive functional groups in the side-chains of said amino acids.

As discussed above, the intermediates of the present invention can be incorporated into peptide chains in a manner utilized in EP-A-97,994. The synthesis method described in EP-A-97,994 pertains to compounds having the formula

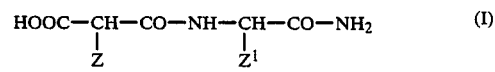

where Z and $Z^1$, which can be the same or different, indicate the side-chain groups of the amino acids commonly present in the natural polypeptide molecules, with final simultaneous release of the entire peptide from the resin, of the terminal $NH_2$ protector groups, and of the functionalities of the amino acid side-chains compatible with the release conditions used, and can be schematized as follows:

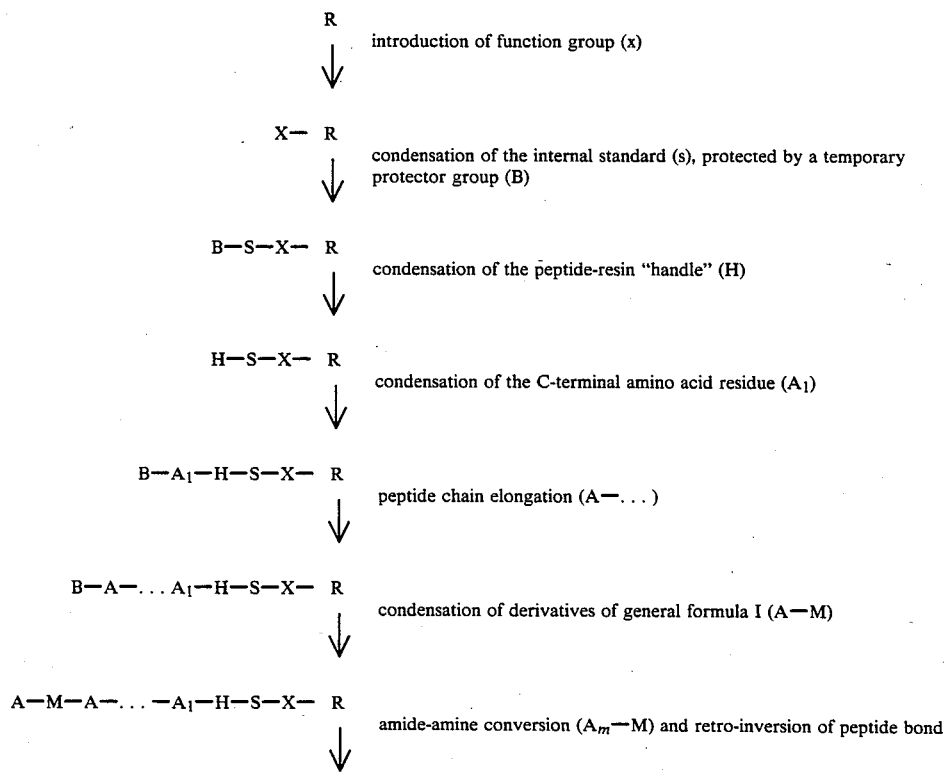

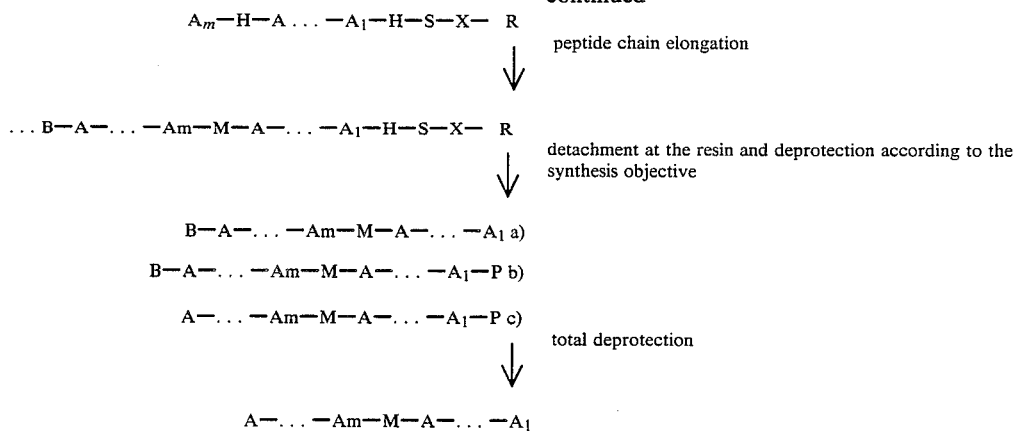

where X=NH₂; S=norleucine residue; H=peptide-resin connection hook; $A_1$=C-terminal amino acid residue; A=amino acid residue; A—M=malonyl or 2-substituted malonyl derivatives of primary amides of D-amino acids; $A_m$=gem-diamino or 2-substituted gem-diamino residue; P=peptide terminal carboxyl protector group; a, b, c=selective release conditions to obtain, respectively, peptides with the amino end protected, peptides with the amino and carboxyl end protected, and peptides with the carboxyl end protected.

The condensation of the products corresponding to general formula (I) is effected using N,N'-dicyclohexylcarbodiimide in the presence of N-hydroxybenzotriazole, or of the preformed symmetrical anhydride. In their turn, the compounds corresponding to general formula (I) can be obtained from a D amino acid primary amide by condensing with a monoester of malonic acid, or of malonic acid substituted in position 2, of general formula:

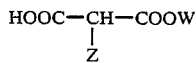

where Z has the meaning given heretofore, and W is methyl, ethyl, benzyl, or t-butyl, in the presence of a suitable condensing agent, preferably N,N'-dicyclohexylcarbodiimide, and N-hydroxybenzotriazole as additive.

The ester protecting group can be removed by catalytic hydrogenation (benzyl ester), by acidolysis (t-butyl ester) or by alkaline hydrolysis (methyl, ethyl and benzyl ester), to obtain the compounds of general formula (I).

The peptides, generally named "retro-inverso" peptides, obtained by reverting the direction of one or more amide bonds of the peptide chain, are structural isomers of the naturally occurring ones. These retro-inverso analogues, which are not topochemically identical to the parent natural peptides, might however retain, either completely or partially, their biological activity or acquire new and more interesting properties owing to the structural variation induced by the reversal of one or more peptide bonds.

Suitable protecting groups (Y) for the different functionalities (amino, carboxyl, hydroxyl and thiol groups), are known in peptide chemistry and are widely described in literature (see for instance R. D. Hey—Organic Chemistry—Series Two—Volume 6—Amino Acids, Peptides and Related Compounds—MTP International Review of Science—Butterworths & Co. Publ.—p.76).

According to a preferred embodiment of the present invention, suitable protecting groups are acid-labile groups i.e. protecting groups which can be easily removed, when desired, by an acidic treatment in mild conditions which do not affect the peptide bonds or remove other protecting groups which are to be retained.

Typically, when an amino function has to be protected, as in the case of the compounds of formula I wherein R is the side-chain residue of a basic amino acid such as lysine or ornithine, suitable protecting groups are, for instance, tert-butoxycarbonyl (Boc), N-2-biphenylyl-2-propoxycarbonyl (Bpoc), tert-amyloxycarbonyl (Aoc), nitrophenylsulphenyl (Nps), and the like, wherein tert-butoxycarbonyl is preferred.

When a carboxyl group has to be protected, as in the case of the compounds of formula I wherein R is the side-chain of an acidic amino acid such as aspartic acid or glutamic acid, protection may suitably be achieved through formation of the corresponding tert-amyl, trityl, di-phenyl-methyl or, preferably, tert-butyl ester. As far as protection of the hydroxyl or thiol functionalities is concerned, trityl, di-phenyl-methyl, tert-amyl, or, preferably tert-butyl groups can suitable be employed.

A preferred group of compounds of the present invention comprises therefore those compounds of formula I wherein R, $R^1$, and $R^2$ are as defined above wherein the protecting groups of the R functionalities are selected from tert-butyl and tert-butoxycarbonyl.

The compounds of the present invention are prepared by methods known in the literature for the preparation of malonic acid derivatives. Said methods are represented in the following Scheme Scheme I

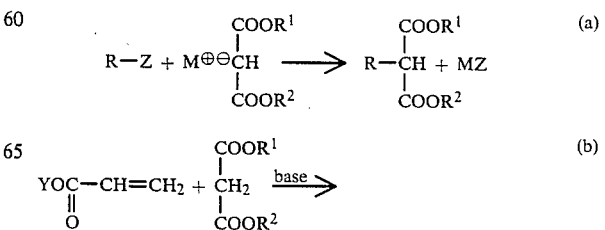

-continued
Scheme I

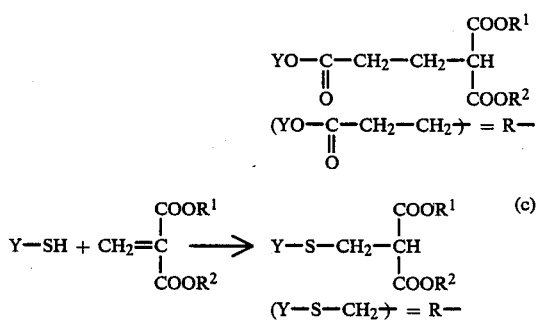

According to reaction (a) of the above scheme, the compound of formula I is obtained by reacting a malonic acid ester alkaline salt, typically malonic acid di-ethyl ester sodium salt, with a halide of the formula RZ wherein R is as defined above and Z is selected from bromo, iodo and chloro, preferably chloro. In particular, this reaction is suitably carried out by preparing first the malonic acid di-ester alkaline salt, e.g. by addition of the malonic acid di-ester to an alkanol solution of the alkali metal, and then adding the reaction partner R-Z to the resulting solution. The reaction smoothly proceeds also at room temperature, but it might be advisable to heat the reaction mixture to the reflux temperature to speed it up. When the reaction, whose course can be easily monitored by thin layer chromatography, is complete, the reaction mixture is washed carefully with water and the organic solvent is evaporated off yielding the compound of formula I as a raw product. The obtained compound can be purified by means of conventional crystallization or distillation techniques of by chromatography, e.g. reverse-phase HPLC.

Reaction (b) of the above scheme, which can be applied to the synthesis of those compounds of formula I wherein the residue R represents the side-chain of glutamic acid (suitably protected at the carboxyl group), provides for the base-catalysed addition of the active methylene group of the malonate to the activated double bond (Michael condensation).

Said addition is carried out by contacting the unsaturated compound YOOC—CH=CH$_2$ with excess malonate in the presence of a polar aprotic organic solvent and of a strong base, such as for instance an alkali metal alcoholate or hydride or a quaternary ammonium hydroxide, which is capable of catalysing the reaction without hydrolysing the ester groups. Also in this case the reaction, whose course may be followed by tlc, is conveniently carried out at room temperature.

At the end of the reaction, conventional working up of the reaction mixture which includes washing it with water and with a buffer or a slightly acidic solution capable of neutralising the base without detaching the protecting group, and evaporating off the organic solvent, yields the compound of formula I wherein R is a group YOOC—CH$_2$—CH$_2$—, as a raw product which may be further purified according to the conventional techniques cited above.

Finally, the compounds of formula I wherein the radical R is the side-chain residue of S-protected cysteine, are conveniently prepared according to reaction (c) of the above scheme which involves addition of the compound Y—SH, wherein Y is a suitably selected thiol-protecting group, to a methylene-malonate. The reaction is carried out by using almost equimolar amounts of the two reactants and contacting them at room temperature in the presence of an aprotic solvent such as water, methanol, ethanol, and the like solvents or their mixtures. At the end of the reaction, unreacted mercaptan, if any, is removed, and an organic solvent poorly miscible with water is added thereto. The desired product of formula I is then recovered from the separated organic phase according to conventional methods and is then purified as described above.

The following examples, which illustrate in detail the preparation of some representative compounds of the invention, should not be interpreted as a limitation to the scope thereof.

EXAMPLE 1

5-[(tert-butoxy)carbonyl]amino-2-ethoxycarbonyl-pentanoic acid ethyl ester (I: $R^1=R^2=Et$; $R=-(CH_2)_3-NHY$; $Y=Boc$)

Sodium metal (2.5 g, 0.1 mol) is dissolved in absolute ethyl alcohol (70 ml) while keeping the reaction mixture under nitrogen atmosphere. The temperature is then brought to 60° C. and malonic acid di-ethyl ester (35 g, 0.2 mol) is gradually dripped in.

N-[(tert-butoxy)carbonyl]-3-chloro-propylamine (12.2 g, 0.1 mol) is gradually added, at room temperature, to the resulting solution. Stirring is continued at room temperature for 2 hours and then at the reflux temperature for 6 hours. The reaction mixture is poured into an ethyl acetate/water (1/1, v/v) mixture (400 ml) and the organic phase is recovered, washed several times with water and dried over MgSO$_4$. The organic solvent is removed under vacuum (0.5 mBar) at 100° C., yielding a pale yellow oil (27.7 g, 87%), N.M.R. analysis of this product confirms the assigned structure.

EXAMPLE 2

6-[(tert-butoxy)carbonyl]amino-2-ethoxycarbonyl-hexanoic acid ethyl ester

I: $R^1=R^2=Et$; $R=-(CH_2)_4-NHY$; $Y=Boc$)

Sodium metal (0.28 g, 0.012 mol) is dissolved in absolute ethyl alcohol (9 ml) under nitrogen atmosphere. The mixture is heated to 60° C. and malonic acid diethyl ester (3.8 g, 0.024 mol) is slowly dripped in.

N-[(tert-butoxy)carbonyl]-4-chloro-butylamine (2.5 g, 0.012 mol) is then gradually added to the resulting mixture at room temperature. The reaction mixture is stirred at room temperature for 2 hours and at the reflux temperature for 6 hours, and then poured into ethyl acetate/water (1/1, v/v) (100 ml). The organic phase is separated, washed several times with water, and dried over MgSO$_4$.

The solvent is then evaporated off under vacuum (0.5 mBar) at 100° C. yielding a raw oily product which is purified by reverse phase HPLC using an RP-18 resin and eluting with an aqueous phase modified with CH$_3$CN (45% by volume). The compound of the title (1.31 g) is thus obtained as a pure product.

EXAMPLE 3

3-[4-benzyloxy-phenyl]-2-ethoxycarbonyl-propionic acid ethyl ester (I: $R^1=R^2=Et$;

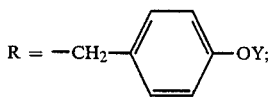

$Y = -CH_2\phi$)

The compound of the title is obtained by following substantially the same procedure as in example 1 but using 4-benzyloxy-benzyl chloride (25 g, 0.1 mol) instead of N-[(tert-butoxy)carbonyl]-3-chloro-propylamine.

The oily product which is obtained is purified by fractional distillation yielding the compound of the title (28.2 g, 80%) as a pure product. B.p. 240° C./0.5 mBar.

The structure of the thus obtained compound is confirmed by NMR and mass spectrometry.

EXAMPLE 4

3-[4-(tert-butoxy)phenyl]-2-ethoxycarbonyl-propionic acid ethyl ester (I: $R^1 = R^2 = Et$;

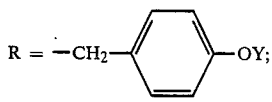

$Y = -C(CH_3)_3$)

The compound of the foregoing example (8.9 g, 0.025 mol) is dissolved in absolute ethyl alcohol (200 ml) in the presence of 10% Pd/C and H$_2$ is bubbled for two hours in the reaction mixture. The reaction mixture is filtered on celite and distilled under vacuum yielding an oily product which is crystallized and washed with a very small amount of n-hexane giving 3-(4-hydroxyphenyl)-2-ethoxycarbonyl-propionic acid ethyl ester (6.3 g) as a crystalline product with m.p. 45° C. This product, methylene chloride (40 ml), and concentrated H$_2$SO$_4$ (3 ml) are charged into a 250-ml glass autoclave and isobutylene (40 ml) cooled to $-85°$ C. is then added thereto.

The reaction mixture is then kept at room temperature, under stirring, for 24 hours.

Excess isobutylene is evaporated off at room temperature, and the residue is taken up in ethyl acetate (300 ml). The resulting organic solution is washed with 5% NaHCO$_3$ (3×100 ml) and then with a saturated NaCl solution (3×100 ml).

The organic solution is dried over MgSO$_4$ and the solvent is evaporated off at room temperature first and then at 100° C. under water pump for 15 minutes, yielding an oil (10 g) which shows four tlc spots in hexane/ethyl acetate (8/2 v/v) (with the following R$_f$: 0.53, 0.38, 0.18, 0.0). The compound with R$_f$ 0.38 is separated by silica gel column chromatography eluting with n-hexane/ethyl acetate (9/1, v/v) yielding 3.7 g (48%) of the compound of the title as a pure product. The analytical data are in complete agreement with the assigned structure.

EXAMPLE 5

1,1,2-ethantricarboxylic acid 2-tert-butyl 1,1-diethyl ester (I: $R^1 = R^2 = Et$; $R = -CH_2-COOY$; $Y = -C(CH_3)_3$)

The compound of the title is prepared by following substantially the same procedure as in example 1 but using bromo-acetic acid tert-butyl ester instead of N-[(tert-butoxy)carbonyl]-3-chloro-propylamine and carrying out the addition at 0° C.

NMR and Mass spectra confirm the assigned structure.

EXAMPLE 6

1,1,3-propantricarboxylic acid 3-tert-butyl 1,1-diethyl ester (I: $R^1 = R^2 = Et$; $R = -CH_2-CH_2-COOY$; $Y = -C(CH_3)_3$)

2-Propenoic acid tert-butyl ester (17 ml, 0.1 mol) is slowly added (6 hours), at room temperature, to a vigorously stirred solution of benzyltrimethylammonium hydroxide (10 ml) and malonic acid di-ethyl ester (40 ml) in dioxane previously dried over aluminum oxide and degassed with helium.

The thus obtained mixture is kept under stirring at room temperature for 24 hours, then it is diluted with CH$_2$Cl$_2$ (150 ml) and washed with water (3×150 ml), 15% citric acid (2×100 ml) and again with water up to neutral reaction.

The organic solution is then dried over MgSO$_4$ and the solvent is removed under vacuum (0.5 mBar) at 100° C. yielding an oily product. Fractional distillation of this product gives the compound of the title (26.4 g) with b.p. 141°–44° C./0.5 mBar. NMR and mass spectra confirm the assigned structure.

EXAMPLE 7

2-[(tert-butoxy)carbonyl]-3-[(tert-butyl)thio]propionic acid ethyl ester (I: $R^1 = Et$; $R^2 = -C(CH_3)_3$; $R = -CH_2SY$; $Y = -C(CH_3)_3$)

Methylenemalonic acid tert-butyl ethyl ester (10 g, 0.05 mol) is slowly (4 hours) added, at room temperature, to a solution of tert-butyl mercaptan (4.5 g, 0.05 mol) in ethanol/water (1/1 v/v).

The reaction mixture is then kept under stirring at room temperature overnight. Unreacted mercaptan is removed by passing a nitrogen stream through the reaction mixture for 8 hours. The reaction mixture is diluted with ethyl acetate/water (2/1 v/v) (150 ml) and the organic phase is separated, washed with 10% NaHCO$_3$ (3×50 ml) and with water up to neutral reaction. The organic solution is then drid over MgSO$_4$ and the solvent is evaporated off under vacuum (0.5 mBar) affording an oily product which is purified by silica gel column chromatography eluting with n-hexane/ethyl acetate (9/1 v/v).

1.31 g of a compound characterized by R$_f$ 0.44 and 0.5 g of a compound characterized by R$_f$ 0.34 (tlc in the same eluting system) are thus obtained.

NMR and mass spectroscopic data confirm that the former compound has the assigned structure, while the latter one should correspond to 2-ethoxycarbonyl-3-(tert-butyl)thio-propionic acid ethyl ester.

EXAMPLE 8

2-(tert-butoxy-carbonyl)-3-(tert-butyl-thio)propionic acid (I: $R^1 = H$; $R^2 = -C(CH_3)_3$; $R = -CH_2-S-Y$; $Y = -C(CH_3)_3$)

A solution of 2-(tert-butoxycarbonyl)-3-(tert-butyl-thio)-propionic acid ethyl ester (1.31 g, 4.5 mmol), prepared according to the procedure of the foregoing example, in tert-butyl mercaptan (8 ml), is slowly (4 hours) added, at room temperature, to a solution of KOH (0.253 g, 4.5 mmol) in absolute ethyl alcohol (4 ml). The reaction mixture is stirred at room temperature overnight and then poured into a mixture of ethyl ether/water (300 ml, 1/1 v/v). The organic phase is separated and extracted with water (3×50 ml). The aqueous phase is acidified with 20% citric acid and then extracted with ethyl acetate (3×100 ml). The organic phase, dried over MgSO₄ and then brought to dryness under water pump, affords 410 mg of the compound of the title. The NMR and mass spectra confirm the assigned structure.

PREPARATION OF THE STARTING COMPOUNDS (a) N-[(tert-butoxy)carbonyl]-3-chloro-propylamine The compound of the title, employed as the starting material in example 1, is prepared by slowly adding a solution of 3-chloro-propylamine hydrochloride (12.98 g, 0.1 mol) in dioxane/water (100 ml 2/1 v/v) to a vigorously stirred mixture of di-(tert-butyl)carbonate (24 g, 0.11 mol), 1N Na₂CO₃ (100 ml) and dioxane/water (200 ml, 2/1 v/v) cooled to 0° C. When the addition is over, the reaction mixture is stirred at room temperature for an additional hour, dioxane is removed under vacuum and the aqueous phase is extracted a few times with ethyl acetate.

From the organic solution an oily product (19.2 g) is recovered, whose structure is confirmed by NMR spectroscopy. This compound can be used as such for the preparation of example 1.

(b) N-[(tert-butoxy)carbonyl]-4-chloro-butylamine

This compound, employed as the starting material in example 2, is prepared by following substantially the same procedure described above under (a) but using 4-chloro-butylamine hydrochloride instead of 3-chloro-propylamine hydrochloride.

(c) Methylenemalonic acid ethyl tert-butyl ester

This compound employed as the starting material in example 7 is prepared as follows: 10% NaOH (2 drops) is added to malonic acid tert-butyl ethyl ester (20 g). Aqueous 40% formaldehyde (15 ml) is then added very slowly thereto while keeping the temperature of the reaction mixture ≦5° C. and the pH at about 8.5 by means of 10% NaOH. The reaction mixture is then stirred at room temperature for 24 hours. The resulting reaction mixture is acidified by the addition of few drops of glacial acetic acid and charged, together with Cu(CH₃COO)₂, into a suitable distilling apparatus.

The fraction distilled in the range 95°–145° C./0.5 mBar is recovered. Mass spectroscopy confirms the assigned structure.

We claim:

1. A compound of the formula:

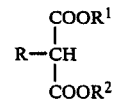

wherein $R^1$ and $R^2$ each independently represent hydrogen atoms, or a straight or branched alkyl group having 2 to 6 carbon atoms or an aralkyl group, and R is selected from the group consisting of
—(CH₂)ₘ—NHY,
wherein, m is 3 or 4 and Y is a tert-butoxy-carbonyl.

2. The compound of claim 1 wherein said straight or branched alkyl group is ethyl, isopropyl, tert-butyl or tert-amyl.

3. The compound of claim 1, wherein said aralkyl group is benzyl, nitro-benzyl, alkoxy-benzyl, or alkyl-benzyl.

4. A compound as in claim 1 which is 5-[(tert-butoxy)carbonyl]amino-2-ethoxycarbonyl-pentanoic acid ethyl ester.

5. A compound as in claim 1 which is 6-[(tert-butoxy)carbonyl]amino-2-ethoxycarbonyl-hexanoic acid ethyl ester.

* * * * *